United States Patent [19]

Shaw

[11] Patent Number: 4,937,258

[45] Date of Patent: Jun. 26, 1990

[54] PYRROLO[1,2-C]IMIDAZOLONE DERIVATIVES AS PDE INHIBITORS

[75] Inventor: Kenneth J. Shaw, Califon, N.J.

[73] Assignee: Berlex Laboratories, Inc., Cedar Knolls, N.J.

[21] Appl. No.: 406,639

[22] Filed: Sep. 12, 1989

[51] Int. Cl.$^5$ .................. A61K 31/415; A61K 31/44; C07D 487/06
[52] U.S. Cl. .................. 514/338; 514/387; 546/271; 548/302
[58] Field of Search .............. 546/271; 548/302; 514/338, 387

[56] References Cited

U.S. PATENT DOCUMENTS 4,582,838 4/1986 Butter et al. .................. 514/322

Primary Examiner—Richard A. Schwartz
Assistant Examiner—Richard A. Sharpe
Attorney, Agent, or Firm—Elizabeth A. Bellamy; John L. White; I. William Millen

[57] ABSTRACT

This invention relates to novel pyrrolo[1,2-c]imidazolones and their pharmaceutically acceptable salts. The compounds of the invention are PDE inhibitors with primarily cardiovascular effects especially cardiotonic effects.

6 Claims, No Drawings

PYRROLO[1,2-C]IMIDAZOLONE DERIVATIVES AS PDE INHIBITORS

FIELD OF INVENTION

This invention relates to novel pyrrolo[1,2-c]imidazolone derivatives and their pharmaceutically acceptable salts. The compounds have demonstrated phosphodiesterase (PDE) inhibition with primarily cardiovascular effects—especially cardiotonic effects. Pharmaceutical compositions containing the compounds are proposed.

GENERAL DESCRIPTION OF THE INVENTION

COMPOSITION-OF-MATTER ASPECT

In its composition-of-matter aspect, this invention relates to novel pyrrolo[1,2-c]imidazolone derivatives and their pharmaceutically acceptable salts.

Compounds encompassed by the invention are of the following Formula I:

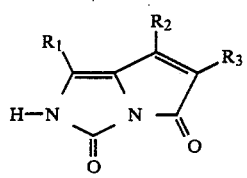

wherein:
$R_1$ is hydrogen, methyl or ethyl;
$R_2$ is 4-pyridyl or

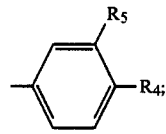

$R_3$ is lower alkyl or phenyl;
$R_4$ is hydrogen, —$SCH_3$, lower alkoxy or

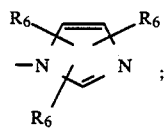

$R_5$ is hydrogen or lower alkoxy;
$R_6$ are the same or different and selected from hydrogen or lower alkyl;
and the pharmaceutically acceptable salts thereof;
with the proviso that $R_4$ and $R_5$ cannot both be hydrogen.

As used herein, the term lower alkyl/alkoxy shall represent a straight chain alkyl of 1 to 4 carbon atoms as for example, methyl, ethyl, propyl and butyl.

Also contemplated as part of this invention are the pharmaceutically acceptable salts of the compounds of Formula I, where such salts are possible. These are acid addition salts and may be formed with inorganic or organic acids. Illustrative but not restrictive examples of such acids include hydrochloric, hydrobromic, sulfuric, phosphoric, citric, acetic, propanoic, benzoic, naphthalenecarboxylic, oxalic, succinic, malic, maleic, adipic, lactic, tartaric, salicyclic, methanesulfonic, 2-hydroxyethanesulfonic, toluenesulfonic, benzenesulfonic, camphorsulfonic and ethanesulfonic acids.

Preferred classes of compounds embodied by this invention are those of the above general Formula I having the characteristics—where $R_1$ is methyl or ethyl and $R_3$ is lower alkyl. Still more preferred compounds are those where $R_1$ is methyl or ethyl and $R_3$ is methyl.

The following compounds are some of those which serve to exemplify the composition-of-matter aspect of this invention.

1,6-Dimethyl-7-[4-(2-methyl-1H-imidazol-1-yl)phenyl]-pyrrolo[1,2-c]imidazole-3,5(2H,6H)-dione.
6-Ethyl-1-methyl-7-[4-(2-methyl-1H-imidazol-1-yl)phenyl]pyrrolo[1,2-c]imidazole-3,5(2H,6H)-dione.
1-Ethyl-6-methyl-7-[4-(2,4-dimethyl-1H-imidazol-1-yl)phenyl]pyrrolo[1,2-c]imidazole-3,5(2H,6H)-dione.
1-Ethyl-6-methyl-7-[4-(2,4,5-trimethyl-1H-imidazol-1-yl)phenyl]pyrrolo[1,2-c]imidazole-3,5(2H,6H)-dione.
1-Ethyl-6-methyl-7-[4-(2-ethyl-1H-imidazol-1-yl)phenyl]pyrrolo[1,2-c]imidazole-3,5(2H,6H)-dione.
1-Ethyl-6-methyl-7-[4-(acetylamino)phenyl]pyrrolo[1,2-c]imidazole-3,5-(2H,6H)-dione.
1-Methyl-6-phenyl-7-(4-pyridinyl)pyrrolo[1,2-c]imidazole-3,5(2H,6H)-dione.
1-Ethyl-6-methyl-7-[3-methoxy-4-(2-methyl-1H-imidazol-1-yl)phenyl]pyrrolo[1,2-c]imidazole-3,5(2H,6H)-dione.

PROCESS ASPECT

The novel pyrrolo[1,2-c]imidazolone derivatives of this invention are prepared essentially via the following Scheme I:

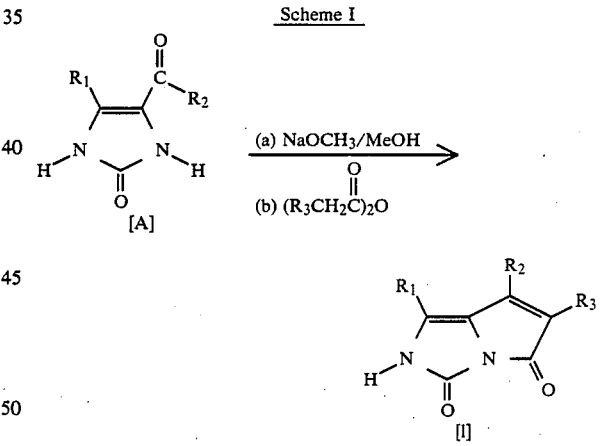

In general, imidazolone derivatives of Formula [A]—as for instance those described in U.S. Pat. No. 4,405,635 and U.S. Pat. No. 4,556,665, are N-acylated followed by a spontaneous cyclic condensation to produce the compounds of Formula [I]. Isolation of the intermediate acyl derivatives—as for instance those described in U.S. Pat. No. 4,743,612, can often be achieved by running the reaction under milder conditions than what is required to effect the specific cyclization. In certain instances these intermediates can then be further cyclized upon reaction under more vigorous conditions.

More particularly, the mono-sodium salts of the imidazolones [A] are prepared first. This is accomplished, in general, by refluxing a mixture of [A] in methanol with 1.0 equivalents of sodium methoxide for about 1 to 3 h. The methanol is removed in vacuo to afford the sodium salt. The sodium salt is alternatively prepared in situ by stirring a suspension of [A] in DMF with 1.0 equivalents of sodium hydride.

The acylation/condensation is generally carried out on the sodium salt with an appropriate anhydride in an aprotic solvent such as DMF, the reaction being run at 20°–80° C. with a time in the range of 16–72 h.

The compounds of the invention are isolated from the resulting mixture of products by a combination of chromatography on silica gel using a $CH_2Cl_2$/MeOH mixture as the eluent followed by recrystallization from acetonitrile, methanol or a mixture of the two.

METHOD OF USE AND PHARMACEUTICAL COMPOSITION ASPECT

The pyrrolo[1,2-c]imidazolones of this invention and their pharmaceutically acceptable salts as disclosed in Formula I are PDE inhibitors primarily in the cardiovascular area. In the cardiovascular area they have been found to be cardiotonic agents with utility in the treatment of congestive heart failure.

The in-vitro screening technique utilized to measure the cardiac c-AMP PDE inhibition of the compounds can be found in J. Med. Chem. 1987 Vol. 30, 1337–1342. Their utility are cardiotonic agents may be determined by using isolated cat or ferret papillary muscle using standard isometric recording techniques. Such a method may be found in J. Med. Chem. 1987, Vol 30, 1342–1347.

In general the compounds of this invention may be administered orally or parenterally. The dosage administered will be dependent on the mammalian host being treated, the route of administration and the magnitude and type of cardiotonic effect to be elicited.

For oral administration the compound to be administered can be formulated by admixing with any number of suitable pharmaceutical diluents and carriers such as lactose, sucrose, starch powder, cellulose, calcium sulfate, sodium benzoate, and the like. Such formulations can be compressed into tablets or encapsulated into gelatin capsules for conventional oral administration.

For parenteral administration a compound of this invention can be formulated, for example, for intramuscular or intravenous administration. Such parenteral administration formulations can be accomplished with any of a number of pharmaceutically acceptable carriers and diluents to constitute an injectable liquid solution. Commonly used diluents and carriers include water or saline solutions, buffered aqueous solutions, including dispersing and surface active agents if necessary.

It is contemplated that in view of the PDE inhibition found with the compounds, that certain of them might prove useful as anti-inflammatory agents, CNS agents, bronchodilators and anti-platelet aggregation agents. Similarly, the cardiac effects found in some of them suggest utility as antiarrhythmic agents.

The invention described hereinabove is illustrated below in the Examples, which, however, is not to be construed as limiting the scope of this invention.

EXAMPLES

EXAMPLE I

1-Ethyl-6-methyl-7-[4-(2-methyl-1H-imidazol-1-yl)phenyl]pyrrolo[1,2-c]imidazole-3,5(2H,6H)-dione 3.65 g of sodium methoxide is added to a suspension of 20.0 g of 4-ethyl-1,3-dihydro-5-[4-(2-methyl-1H-imidazol-1-yl)benzoyl]-2H-imidazol-2-one in 1 liter of anhydrous methanol. The mixture is refluxed for 1 h, then cooled to room temperature. The methanol is removed with a rotoevaporator and the resultant solid dried in vacuo to afford the sodium salt.

The sodium salt is added to a solution of 13.2 g of propionic anhydride in 700 mL anhydrous DMF. The reaction mixture is heated at 75° C. with stirring for 18 h under a nitrogen atmosphere. The reaction mixture is cooled to room temperature and the solids collected by filtration. Recrystallization from acetonitrile affords the title compound.

NMR (DMSO-$d_6$) $\delta$=1.06(t, 3H), 1.87(s, 3H), 2.28(q, 2H), 2.36(s, 3H), 6.99(s, 1H), 7.43(s, 1H), 7.65(m, 4H), 10.72(s, 1H).

EXAMPLE II

1-Ethyl-6-phenyl-7-[4-(2-methyl-1H-imidazol-1-yl)phenyl]pyrrolo[1,2-c]imidazole-3,5(2H,6H)-dione 0.97 g of sodium methoxide is added to a suspension of 5.3 g of 4-ethyl-1,3-dihydro-5-[4-(2-methyl-1H-imidazol-1-yl)benzoyl]-2H-imidazol-2-one in 250 mL of anhydrous methanol. The mixture is refluxed for 1 h then cooled to room temperature. The methanol is removed with a rotoevaporator and the resultant solid is dried in vacuo to afford the sodium salt.

The sodium salt is suspended in 150 mL of anhydrous DMF to which is added 6.8 g of phenylacetic anhydride. The reaction mixture is stirred at room temperature for 4.5 h under a nitrogen atmosphere. The DMF is then removed by distillation in vacuo (50°, 1 mm). The residue is partitioned between 200 mL of 1M methanesulfonic acid and 300 mL dichloromethane. The organic layer is extracted twice with 50 mL of 1M methanesulfonic acid, and the combined acid extracts are brought to a pH=9 with concentrated ammonium hydroxide. The mixture is filtered and the filtrate is extracted five times with 150 mL portions of dichloromethane. The combined dichloromethane extracts are dried with magnesium sulfate and filtered. To the filtrate is added 15 g of silica gel, the solvent is then removed in vacuo and the adsorbed solid is dried in vacuo and then added on top of a silica gel column and eluted with a mixture of dichloromethane:methanol, 94:6 to afford the title compound.

NMR (DMSO, $d_6$) $\delta$=1.08(t, 3H), 2.27(quar, 2H), 2.33(s, 3H), 6.95(d, 1H), 7.22–7.38(m, 5H), 7.40(d, 1H), 7.52–7.61(m, 4H), 11.00(br s, 1H).

EXAMPLE III

1-Ethyl-6-methyl-7-[4-(1H-imidazol-1-yl)phenyl]pyrrolo[1,2-c]imidazole-3,5(2H,6H)-dione 2.87 g of sodium methoxide is added to a suspension of 15.0 g of 4-ethyl-1,3-dihydro-5-[4-(1H-imidazol-2-yl)benzoyl]-2H-imidazol-2-one in 750 mL of anhydrous methanol. The mixture is refluxed for 1 h, then cooled to room temperature. The methanol is removed with a rotoevaporator and the resultant solid dried in vacuo to afford the sodium salt.

The sodium salt is suspended in 350 mL of anhydrous DMF and to this mixture is added 10.0 g of propionic anhydride. The reaction mixture is heated at 55° C. with stirring for 48 h under a nitrogen atmosphere. The reaction mixture is then cooled to room temperature and the DMF is removed by distillation in vacuo (50° C., 1 mm). The residue is chromatographed on silica gel, eluting with a mixture of dichloromethane:methanol, 95:5 to afford the title compound.

NMR (DMSO-d$_6$) δ=1.06(t, 3H), 1.86(s, 3H), 2.27(q, 2H), 7.15(s, 1H), 7.63(d, 2H), 7.85(m, 3H), 8.40(s, 1H), 10.70(s, 1H).

EXAMPLE IV

1-Ethyl-6-methyl-7-[4-(methylthio)phenyl]pyrrolo[1,2-c]imidazole-3,5(2H,6H)-dione 2.10 g of sodium methoxide is added to a suspension of 10.2 g of 4-ethyl-1,3-dihydro-5-[4-(methylthio)benzoyl]-2H-imidazol-2-one in 500 mL of anhydrous methanol. The mixture is refluxed for 1 h, then cooled to room temperature. The methanol is removed with a rotorevaporator and the resultant solid dried in vacuo to afford the sodium salt.

The sodium salt is suspended in 250 mL of anhydrous DMF, and to this mixture is added 7.9 g of propionic anhydride. The reaction mixture is heated at 65° C. with stirring for 18 h under a nitrogen atmosphere. The reaction mixture is then cooled to room temperature and the DMF is removed by distillation in vacuo (50° C., 1 mm). The residue is chromatographed on silica gel eluting with a mixture of dichloromethane:methanol, 97:3 to afford the title compound.

NMR (DMSO-d$_6$) δ=1.05(t, 3H), 1.83(s, 3H), 2.25(q, 2H), 2.53(s, 3H), 7.41(m, 4H), 10.63(br s, 1H).

I claim:

1. A compound of the following Formula I:

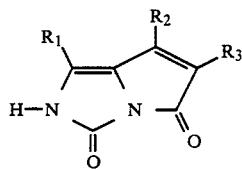

I wherein:

$R_1$ is hydrogen, methyl or ethyl;
$R_2$ is 4-pyridyl or

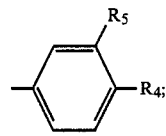

$R_3$ is lower alkyl or phenyl;
$R_4$ is hydrogen, —SCH$_3$, lower alkoxy or

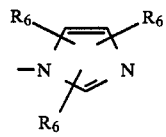

$R_5$ is hydrogen or lower alkoxy;
$R_6$ are the same or different and selected from hydrogen or lower alkyl or the pharmaceutically acceptable salt thereof; with the proviso that $R_4$ and $R_5$ cannot both be hydrogen.

2. A compound of claim 1 which is 1-ethyl-6-methyl-7-[4-(2-methyl-1H-imidazol-1-yl)phenyl]pyrrolo[1,2-c]imidazole-3,5(2H,6H)-dione.

3. A compound of claim 1 which is 1-ethyl-6-methyl-7-[4-(1H-imidazol-1-yl)phenyl]pyrrolo[1,2-c]imidazole-3,5(2H,6H)-dione.

4. A compound of claim 1 which is 1-ethyl-6-phenyl-7-[4-(2-methyl-1H-imidazol-1-yl)phenyl]pyrrolo[1,2-c]imidazole-3,5(2H,6H)-dione.

5. A compound of claim 1 which is 1-ethyl-6-methyl-7-[4-(methylthio)phenyl]pyrrolo[1,2-c]imidazole-3,5(2H,6H)-dione.

6. A pharmaceutical composition comprising an effective amount of a compound according to claim 1, together with one or more non-toxic pharmaceutically acceptable carriers.

* * * * *